(12) United States Patent
Lundkvist et al.

(10) Patent No.: US 10,010,371 B2
(45) Date of Patent: Jul. 3, 2018

(54) SAMPLING SYSTEM

(71) Applicant: APROVIX AB, Uppsala (SE)

(72) Inventors: Ulf Lundkvist, Uppsala (SE); Berndt Sjoberg, Sodertajle (SE); Erik Wilander, Uppsala (SE); Soren Nygren, Åkersberga (SE); Lars Ivarsson, Stockholm (SE)

(73) Assignee: Aprovix AB, Uppsala (SE)

( * ) Notice: Subject to any disclaimer, the term of this patent is extended or adjusted under 35 U.S.C. 154(b) by 336 days.

(21) Appl. No.: 14/697,780

(22) Filed: Apr. 28, 2015

(65) Prior Publication Data

US 2015/0230872 A1 Aug. 20, 2015

Related U.S. Application Data

(63) Continuation-in-part of application No. 14/072,969, filed on Nov. 6, 2013, now Pat. No. 9,060,753, which
(Continued)

(51) Int. Cl.
| | |
|---|---|
| *A61B 10/00* | (2006.01) |
| *A61B 19/00* | (2006.01) |
| *A61B 10/02* | (2006.01) |
| *A61B 90/98* | (2016.01) |
| *A61B 90/96* | (2016.01) |

(Continued)

(52) U.S. Cl.
CPC .......... *A61B 19/44* (2013.01); *A61B 10/0096* (2013.01); *A61B 10/0291* (2013.01); *A61B 10/0038* (2013.01); *A61B 10/0045* (2013.01); *A61B 10/0051* (2013.01); *A61B 90/90* (2016.02); *A61B 90/96* (2016.02); *A61B 90/98* (2016.02); *A61B 2010/0074* (2013.01); *A61B 2010/0216* (2013.01); *A61B 2017/0046* (2013.01); *A61B 2017/00473* (2013.01); *A61B 2019/448* (2013.01)

(58) Field of Classification Search
CPC ............ A61B 10/0291; A61B 10/0045; A61B 10/0051; A61B 10/0096; A61B 10/0038; A61B 2010/0216; A61B 2010/0074; A61B 2017/0046; A61B 2017/00473; A61B 90/90; A61B 90/96; A61B 90/98; C12M 33/02; G01N 2001/005; G01N 2001/007; B01L 2300/021; B01L 2300/022

See application file for complete search history.

(56) References Cited

U.S. PATENT DOCUMENTS

| 9,060,753 B2 * | 6/2015 | Lundkvist .......... A61B 10/0096 |
| 2003/0028123 A1 * | 2/2003 | Pevoto ............... A61B 10/0045 600/562 |

(Continued)

*Primary Examiner* — Devin Henson
(74) *Attorney, Agent, or Firm* — Berggren LLP; Leea Somersalo

(57) ABSTRACT

A sampling system for an individual to self-collect sample form mucous tissue is disclosed here. The collecting device has a flexible shaft having a handle at one end, and a sample collecting element removably connectable with the other end of the shaft and operable to collect a cell sample from mucous tissue of an individual. The collecting element includes an RFID tag for tracking the device and the sample once it is collected onto the collecting element. The system includes a sealable unit to store the sample collecting element having a cell sample thereon.

14 Claims, 14 Drawing Sheets

Related U.S. Application Data is a continuation of application No. 11/920,462, filed as application No. PCT/IB2006/001723 on May 26, 2006, now abandoned.

(60) Provisional application No. 60/685,892, filed on May 31, 2005.

(51) Int. Cl.
  *A61B 17/00* (2006.01)
  *A61B 90/90* (2016.01)

(56) References Cited

U.S. PATENT DOCUMENTS

| | | | | |
|---|---|---|---|---|
| 2005/0205673 | A1* | 9/2005 | Morris | B01L 3/5027 235/385 |
| 2007/0244470 | A1* | 10/2007 | Barker, Jr. | A61B 90/98 606/1 |
| 2010/0032437 | A1* | 2/2010 | Lossau | B01L 3/545 220/694 |
| 2010/0063847 | A1* | 3/2010 | Eisenberg | A61B 10/0096 705/3 |
| 2010/0160830 | A1* | 6/2010 | Schmiedl | A61B 10/0045 600/572 |
| 2011/0172557 | A1* | 7/2011 | Lonky | A61B 10/02 600/569 |
| 2012/0310113 | A1* | 12/2012 | Giddings | A61B 10/0051 600/570 |

* cited by examiner

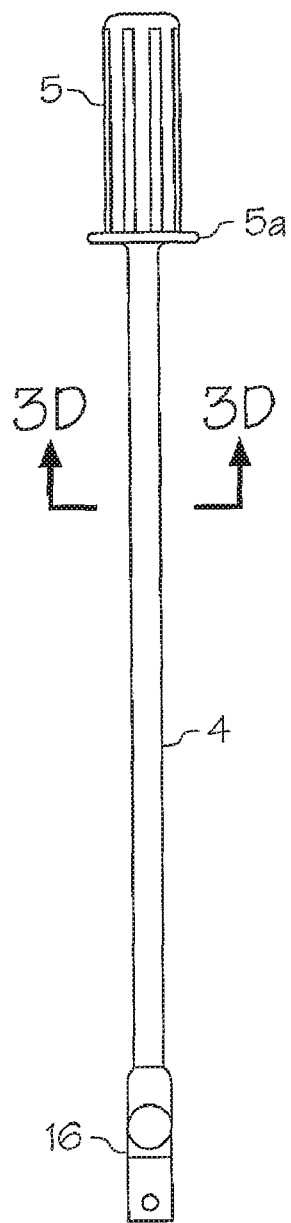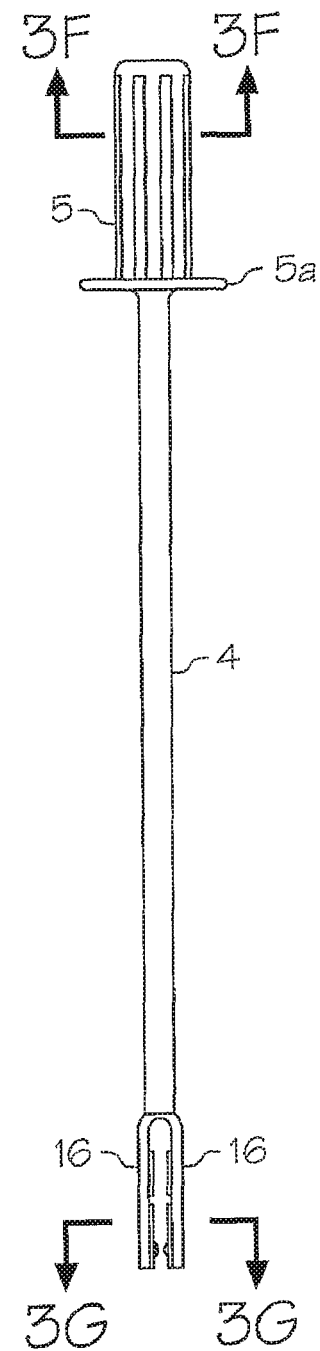
FIG. 3C
FIG. 3E

SAMPLING SYSTEM

PRIORITY CLAIM

This application is continuation in part of U.S. patent application Ser. No. 14/072,969, which was filed on Nov. 6, 2013, and claimed priority of U.S. Ser. No. 11/920,462, filed on Nov. 15, 2007 and which was a national application of PCT/IB2006/001723 filed on May 26, 2006 and which claimed priority of U.S. 60/685,892 filed on May 31, 2005. The contents of each of which are incorporated herein by reference in their entirety.

FIELD OF THE INVENTION

The present invention relates generally to the field of screening and health control. More specifically the invention relates to a novel sampling system and improved tracking of samples and associated methods suitable, for example, in testing to detect virus-associated cervical cancer, microbial infections and pathological changes.

BACKGROUND OF THE INVENTION

Cervical cancer is the second most common form of cancer in women world-wide.

Invasive cervical carcinoma develops by progression of less severe epithelial changes, known as dysplacia and cervical intraepithelial neoplacia (CIN I-II-III), into cervical carcinomas in situ (CIS).

Using vaginal aspirates (Pap smears), the epithelial changes can be detected and classified by common cytological methods. It is particularly important to notice that invasive cervical carcinoma is preceded by its dysplastic precursor lesions, which can be present for months or years before cervical carcinoma develops. Furthermore, progression to carcinoma can effectively be stopped by a simple operation (conization) if the precursor lesions are detected.

Many developed countries have experienced up to a 50% reduction in the incidence of and mortality from invasive cervical carcinoma after the introduction of organized screening programs. Despite this fact, about 500,000 women in the world are struck by cervical cancer each year. In the U.S., close to 5,000 women die each year from this disease. This number would drop further if more women were tested on a regular basis.

Of those who die of cervical cancer, 50% have not had a Pap test done in 5 or more years. Indeed, those women who do not participate in the gynecological health control and those who show false negative cytology are the highest risk groups for cervical cancer. The efficacy and reliability of the sampling method and the sample's analysis are therefore primary issues. This involves, in the first place, reaching those women who do not now participate in the gynecological screening by providing a simple and reliable device for sampling, and secondly, to increase the discriminating efficacy of the analytical methods to diagnose infections, precancerous lesions or cancerous lesions.

Association between papillomavirus (HPV) infection and cervical carcinoma was postulated in the 1970's. The International Biological Study on Cervical Cancer reported a world-wide prevalence of infection with HPV of 93% in women with invasive cervical cancer. In addition, the subtypes HPV 16 and HPV 18 are the most significant risk factors in its etiology. HPV infection is also an important risk factor for progression of CIN.

Recent studies with improved methods of polymerase chain reaction (PCR) imply an overall HPV prevalence of almost 100% and that the PCR results correlate with the histological findings. These results reinforce the rational for HPV testing in combination with, or even instead of, cytology in population-based screening programs.

Determination of squamous intraepithelial lesions, or cervical dysplasia, is commonly used as an indication of progression to cervical cancer. Alternatively, the presence of HPV nucleic acid in a patient sample, following amplification by PCR, is taken as a risk factor for progression to cervical cancer. From the above, it is obvious that cytology and PCR analysis of HPV infection provide very efficient means to detect individuals at risk to develop cervical cancer.

Recently published evidence-based consensus guidelines for the management of women with cervical cytological abnormalities and cervical cancer precursors state that women with atypical squamous cells of undetermined significance (ASCUS) should be managed using a program of 2 repeat cytology tests, immediate colposcopy, or DNA testing for high-risk types of HPV. Testing for HPV DNA is the preferred approach when liquid-based cytology is used for screening.

The limiting factor in order to further decrease the incidence of and mortality from cervical cancer appears therefore to be related to reaching the non attending women and providing a simple sampling device giving relevant samples for HPV analysis and/or cytology.

Traditionally, sampling of vaginal smear requires scraping of a woman's cervix with a sampling device, such as a spatula or a brush. This sampling is generally performed by medical professionals like gynecologists, midwifes or nurses in a clinical environment. Many women, who now refrain from such gynecological testing, would participate if the sampling could be carried out at home and/or by the women themselves. Self and home sampling would therefore increase the participation in the gynecological screening, and by that means, decrease the incidence of cervical cancer.

US2003/0028123 discloses intra-vaginal self-administered cell collection device, but no snap-fit connection.

US 5,445 A disclose a quick-release connection in the context of a cervical tissue sampling device, but the release mechanism is based on sliding a sleeve rewardly along shaft until engaged tab end portions are exposed. The pin may then be manually disengaged from aperture to complete detachment of stem from shaft.

In addition to the above, sampling systems are also in demand for DNA analysis. Law enforcement officials, paternity agents, etc. are constantly taking DNA samples to help solve crimes, determine paternity, etc. As the results of the tests done on these samples dramatically affect people's lives and may be desired as evidence in legal proceedings, the sampling must be done in a manner in which the sample contamination is reduced or avoided. As such, there is a need for an improved sampling system.

Furthermore, there is a need for improved tracking methods of samples to avoid mixing the samples or losing the identity of a sample.

SUMMARY OF THE INVENTION

In view of the need for an improved sampling device and a system easily adaptable to present health screening procedures, and for easy and reliable tracking system, the present invention therefore provides improvement over the currently available devices and systems.

In one embodiment, the present invention comprises a sampling system comprising: a) a mailing package; and b) a sampling device consisting of: a flexible linear shaft configured to allow an individual to self-collect a sample from mucous tissue, said shaft having a first end and a second end and a handle at the first end and a longitudinal axis extending from the first end to the second end, and the second end having a shaft extension with two perpendicular prongs, each prong having in its inner surface a groove and a protrusion, said grooves being on same level at a proximal end of the forks and said protrusions being on same level at a distal end of the forks; a detachable cylindrical sample collecting element having a rounded distal end and a collection element extension at a proximate end, the collection element extension dimensioned to fit in between the two prongs of the shaft extension and having protrusions on its opposite sides fitting in the grooves of the shaft extension, wherein the sample collecting element is connected to the shaft extension by snapping the collecting element extension in between the forks of the shaft extension and aligning the protrusions of the collecting element extension with the grooves on the forks, the collecting element having an RFID-tag comprising of an RFID-chip and an antenna; and wherein the collecting element can be disconnected from the shaft extension by pivoting the shaft in relation to the collection element at connection of shaft extension and collection element extension to release the protrusions of the collection element extension from the grooves on the forks, and wherein the collecting element has a surface formed of raised portions and grooves; and a sealable unit, wherein the unit is configured to store the sample collecting element, disconnected from the shaft and having a sample thereon, in a sealed form and to be received within the mailing package in a selected form.

In one embodiment, the present invention comprises a sampling system comprising: a) a mailing package; and b) a sampling device consisting of: a flexible linear shaft configured to allow an individual to self-collect a sample from mucous tissue, said shaft having a first end and a second end and a handle at the first end and a longitudinal axis extending from the first end to the second end, and the second end having a shaft extension with two perpendicular prongs, each prong having in its inner surface a groove and a protrusion, said grooves being on same level at a proximal end of the forks and said protrusions being on same level at a distal end of the forks; a detachable cylindrical sample collecting element having a rounded distal end and a collection element extension at a proximate end, the collection element extension dimensioned to fit in between the two prongs of the shaft extension and having protrusions on its opposite sides fitting in the grooves of the shaft extension, wherein the sample collecting element is connected to the shaft extension by snapping the collecting element extension in between the forks of the shaft extension and aligning the protrusions of the collecting element extension with the grooves on the forks, the collecting element extension further having at least one cavity for adapting an RFID-tag; and wherein the collecting element can be disconnected from the shaft extension by pivoting the shaft in relation to the collection element at connection of shaft extension and collection element extension to release the protrusions of the collection element extension from the grooves on the forks, and wherein the collecting element has a surface formed of raised portions and grooves; and a sealable unit, wherein the unit is configured to store the sample collecting element, disconnected from the shaft and having a sample thereon, in a sealed form and to be received within the mailing package in a selected form.

In another embodiment, the present invention comprises a sampling system comprising: a) a mailing package; and b) a cell sampling device consisting of: a flexible linear shaft configured to allow an individual to self-collect a sample from mucous tissue, said shaft having a first end and a second end and a handle at the first end and a longitudinal axis extending from the first end to the second end, and the second end having a shaft extension with two perpendicular prongs, each prong having in its inner surface a groove and a protrusion, said grooves being on same level at a proximal end of the forks and said protrusions being on same level at a distal end of the forks; a detachable cylindrical sample collecting element having a rounded distal end and a collection element extension at a proximate end, the collection element extension dimensioned to fit in between the two prongs of the shaft extension and having two protrusions on its opposite sides fitting in the grooves of the shaft extension, wherein the sample collecting element is connected to the shaft extension by snapping the collecting element extension in between the forks of the shaft extension and aligning the protrusions of the collecting element extension with the grooves on the forks, wherein the cylindrical sample collecting element contains an embedded RFID-tag; and wherein the collecting element can be disconnected from the shaft extension by pivoting the shaft in relation to the collection element at connection of shaft extension and collection element extension to release the protrusions of the collection element extension from the grooves on the forks, and wherein the collecting element has a surface formed of raised portions and grooves; and a sealable unit, wherein the unit is configured to store the sample collecting element, disconnected from the shaft and having a sample thereon, in a sealed form and to be received within the mailing package in a selected form.

According to one embodiment the RFID-tag embedded inside the cylindrical sample collecting element.

According to one embodiment the RFID-tag is injection molded inside the sample collecting element.

According to one embodiment the RFID-tag contains an UHF-RFID chip that may be read from a distance up to several meters, thereby enabling reading several devices at one reading.

According to one embodiment the RFID tag may be read one by one with a smart phone using near field communication technologies (NFC).

According to one embodiment a logistic method for gynecological samples is provided. The method comprises the steps of providing to a healthcare unit a multitude of sampling devices as described in this disclosure with prewritten RFID-tags, said prewritten tags comprising information to identify each device; the healthcare unit reading the information and entering the information into a database; the healthcare unit adding information of a multitude of individuals on the database and correlating one device with one individual; the healthcare unit sending each device to the individual correlated with the device; the individual, upon receive of the device, self-sampling a gynecological sample, inserting the sample collecting element into the sealable unit and sending the sealable unit back to the healthcare unit; the healthcare unit collecting all received sealable units in single container and sending the container to a laboratory; the laboratory reading the information of all the received sealable units with one reading of the RFID-tags; the laboratory entering the read information into their database; the laboratory analyzing the samples and entering the results into the database by correlating one result with one device information; the laboratory sending the information in the database to the healthcare unit; the healthcare unit correlating each result with individuals based on the device information; and the healthcare unit informing each individual of her result.

The sampling systems of the invention may be used by medical personnel in doctor's offices, health clinics, or hospitals, for patient sampling and/or may be used by individuals for self-sampling. In addition, the sampling system lends itself and maybe used by other personnel in other settings, for example in rural areas where no equipment is available, and where the RFID-tags can be read by using a smartphone. The sampling systems are particularly advantageous for use by an individual in conduct self-sampling in testing to detect, for example, virus-associated cervical cancer, microbial infections and pathological changes. These and additional embodiments and advantages may be more fully apparent in view of the detailed description.

BRIEF DESCRIPTION OF THE DRAWINGS

The present invention will be better understood from the detailed description, given herein below and the accompanying drawings which are given for illustration, and thus not limiting the scope of the invention, and wherein:

FIGS. 3A-3J show schematic plan and cross-sectional views of a sampling device included in one embodiment of a sampling system according to the invention.

DETAILED DESCRIPTION

Figure 1A:
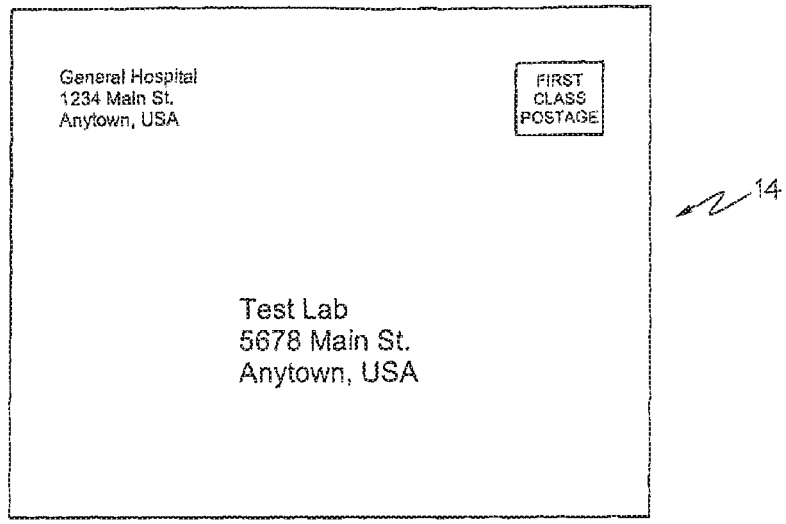
FIGS. 1A and 1B are, respectively, a front view of mailing package and a rear view of a bar-coded transport package included in one embodiment of the sampling system according to the invention.
Figure 1B:
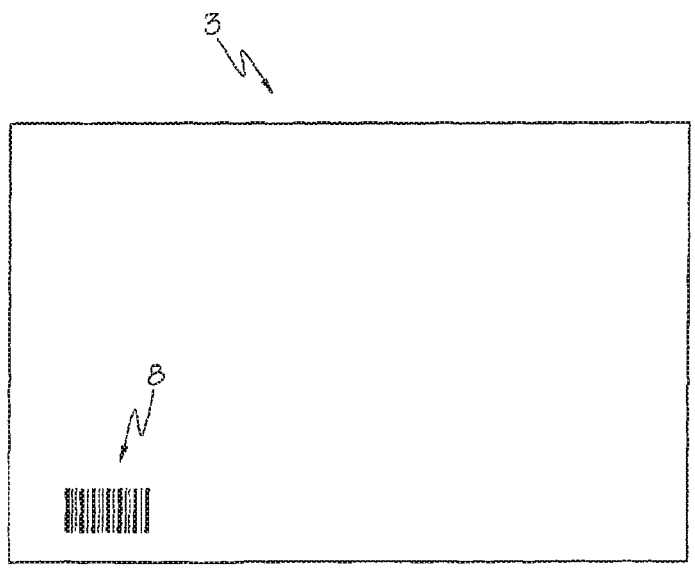

Definitions: By RFID tag it is meant an RFID transponder that can communicate with a computer via electromagnetic field between the antennas of the tag and the reader unit (computer controlled transmitter/receiver). By RFID chip it is meant the electronics of the tag without the antenna.

The present invention provides a sampling system that overcomes disadvantages of prior art devices, instruments and procedures for obtaining samples from mucous tissue such as, but not limited to, the gynecological tract and the mouth. The invention provides also a reliable tracking system for the sampling devices and sample collecting elements before and after sampling. The invention provides a system to track and identify the samples from point of sampling to the analyzing of the samples. The ID is at all times traveling with the sample.

In a first aspect, the present invention provides a sampling system which may be employed by an individual to easily and reliably, at home or at a visit to a medical location, under hygienic conditions, take cell smears and samples, for example, gynecological samples, from mucous tissues. The samples can be transported without risk of contamination or transmission of infective agents, and thereafter be analyzed by chemical methods, such as PCR, or by other microbiological methods. The device carries an identification system that allows tracking of the devices or the sample collecting elements before and after sampling.

With reference to FIGS. 1-11, the sampling system according to one embodiment of the present invention includes a sampling device 2 for taking cell samples, a mailing package 14 for returning a sample to, for example, a laboratory for testing, and a sealable unit 7. Optionally, the sampling system may include a transport package 3 for delivery of the sampling system components to a user. One embodiment of the transport package 3 is shown in FIG. 1B, and includes a bar code, for use as described in further detail below. One embodiment of the mailing package 14, including a printed address for mailing a sample to the appropriate medical professional, on the front side thereof is shown in FIG. 1A. It will be appreciated that the transport package 3 and the mailing package 14 may be provided with this exemplary information, or other information as desired, in any suitable arrangement. The mailing package 14 allows return of the sealable unit 7 and contents thereof to the appropriate facility, for example, by mail, courier or the like, without compromising the sealable unit or its contents.

In another embodiment the identification of the barcode may be omitted when the self-sampling device 2 is constructed so as to include an identification system, preferably an RFID tag in itself. This embodiment is described in more details below and shown in details in FIGS. 5-11.

In one embodiment, the cell sampling device 2 comprises a shaft 4 having a handle 5 at one end. The handle may include a lower lip 5 as shown to facilitate the ease of use of the device. The shaft 4 is configured to allow an individual to self-collect a sample from mucous tissue. In a specific embodiment, the shaft 4 is configured to allow an individual to self-collect a gynecological sample from a cervix location. In an additional embodiment, at least a portion of the shaft is flexible, and in a further embodiment, a portion of the shaft 4 is rigid. Alternatively, the shaft may be entirely flexible. Reference to a flexible shaft is intended to mean at least a portion of the shaft is flexible, in another embodiment, the shaft 4 is formed of a polymer, including, for example, polypropylene, polyethylene, or a mixture thereof.

Figure 3A:
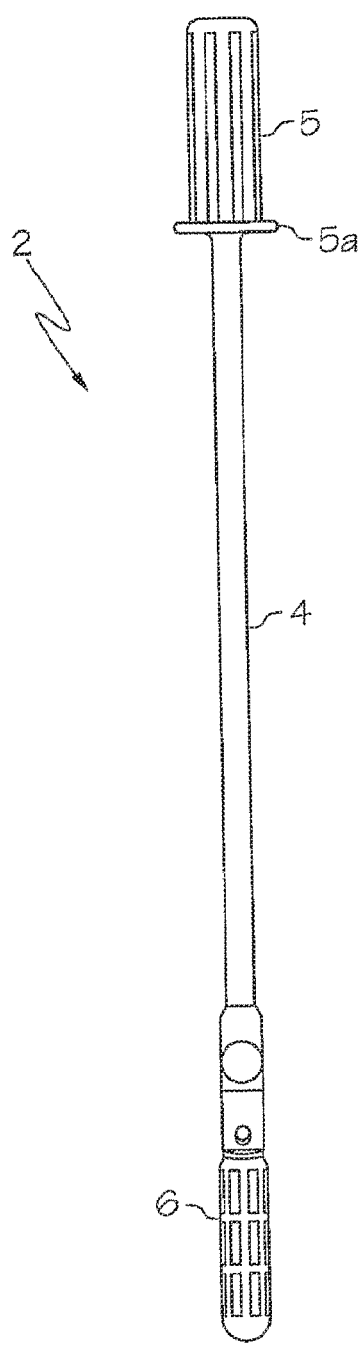
Figure 3B:
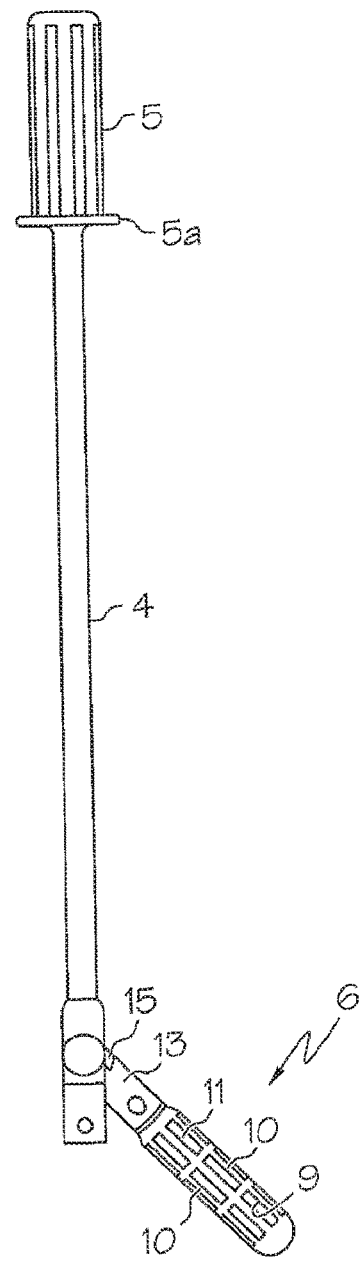
Figure 3D:
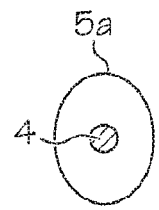
Figure 3F:
Figure 3G:
Figure 3H:
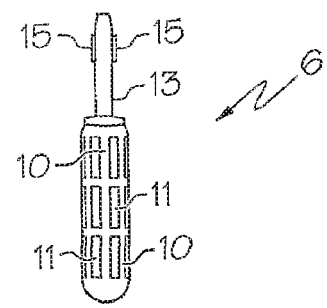
Figure 3I:
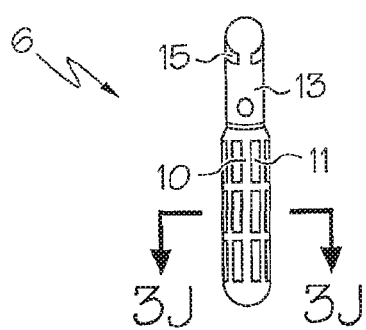
Figure 3J:
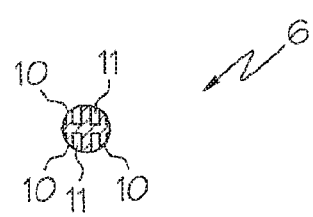

The sampling device 2 further comprises a sample collecting element 6 removably connectable with the other end of the shaft 4 opposite the handle. The element 6 is operable to collect a cell sample from mucous tissue of an individual. FIGS. 3A and 3B show the sample collecting element 6 removably connected with the shaft 4, while FIGS. 3C and 3E show the shaft 4 without the sample collecting element 6 thereon and FIGS. 3H and 3I show the sample collecting element 6 apart from the shaft 4. FIG. 3D shows a cross-sectional view taken along line D-D in FIG. 3C; FIGS. 3F and 3G show cross-sectional views taken along lines F-F and G-G in FIG. 3E, respectively, and FIG. 3J shows a cross-sectional view taking along line J-J in FIG. 3I.

The sealable unit 7 is configured to store the sample collection element 6 having a cell sample thereon, preferably in a manner which prevents contamination of the element 6, i.e., in an air tight manner, and to be received within the mailing package 14 in its sealed form. In one specific embodiment, the unit 7 is a sealable tube.

In an additional embodiment, the transport package 3 and the unit 7 each have an identification element 8, for example correlating to the individual from which a sample is made. In a further embodiment, the identification element 8 consists of a bar code.

Figure 5A:
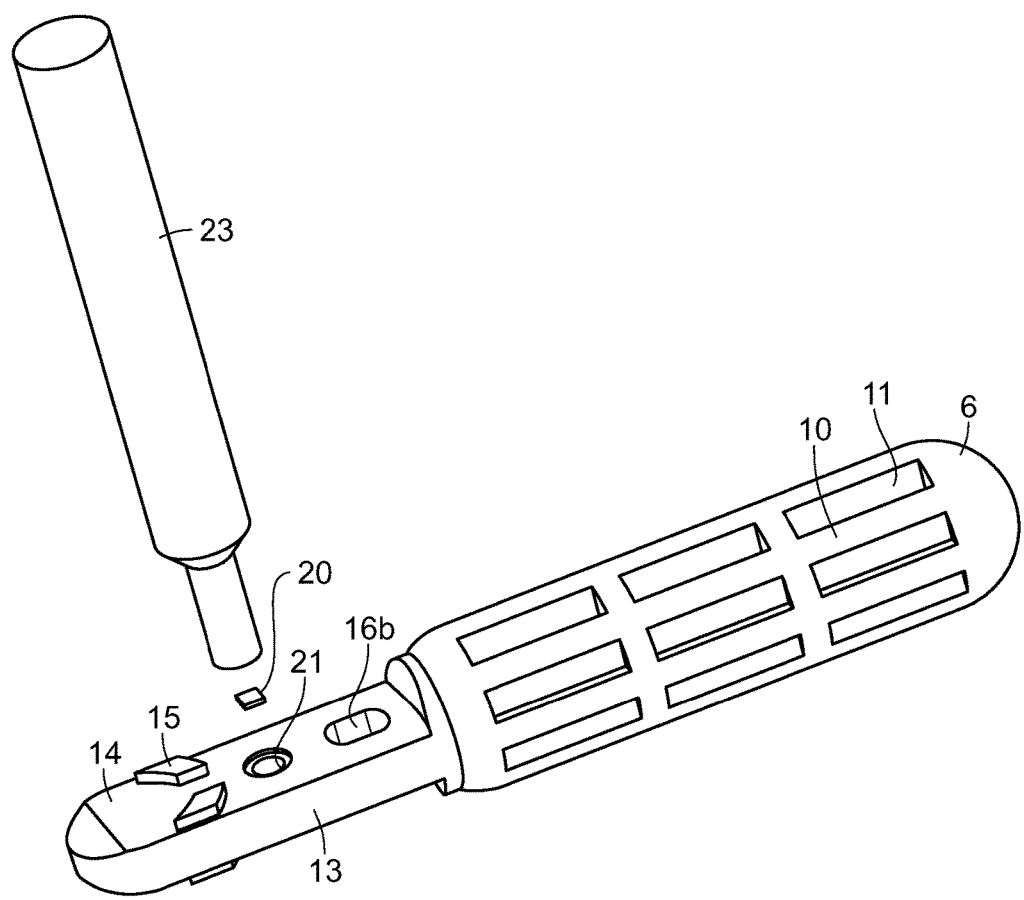
FIG. 5 A and B show an illustration of inserting an RFID tag into a cavity on the extension of the collecting element extension. A) is a three dimensional illustration, while B) is two dimensional illustration of the same.

In a further embodiment of the invention the identification element locates in the self-sampling device. According to this embodiment the identification element uses RFID technology. According to this embodiment the identification element may locate in the extension 13 of the collecting element 6 as shown in FIG. 5A and B. The identification element in this embodiment is an RFID tag 20. In FIG. 5A and B the RFID tag 20 is inserted in a cavity 21 that is on a flat surface 14 of the extension 13 of the collecting element 6. In one preferred embodiment the extension of the collecting element is flat and has two flat surfaces. In this embodiment there are two cavities on the extension: one cavity on each flat side. The RFID tag may be inserted into either one of the cavities. Having one cavity on each flat surface helps fast attachment of the RFID-tag because there is no need to orientate the sample collecting element but the tag goes on either side of the flat extension. According to one embodiment the two cavities may be connected by a hole through the flat colleting element extension. FIG. 5A and B also show a heated fixation tool 23 to attach the tag on the device. The tool provides high enough temperature to mold the tag onto the cavity.

The RFID tag may be molded on the extension 13 by for example injection mold process. Because the temperature during molding is high, the RFID electronics may be for example on ceramic PCB.

Figure 6A:
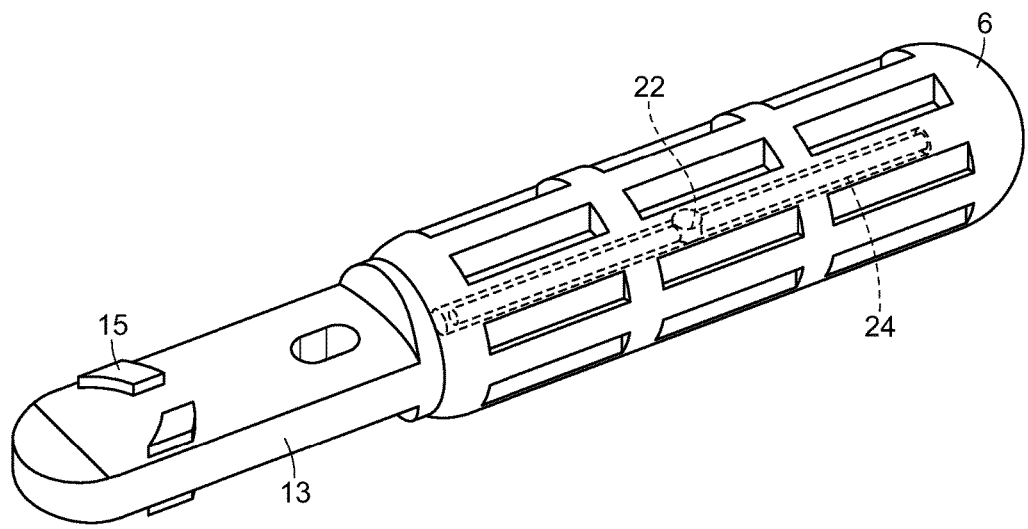
FIG. 6 A and B show an illustration of one embodiment of an RFID tag inside the collecting element, where the RFID chip is on a thin metal wire antenna. A) is a three dimensional illustration, while B) is two dimensional illustration of the same.
Figure 6B:
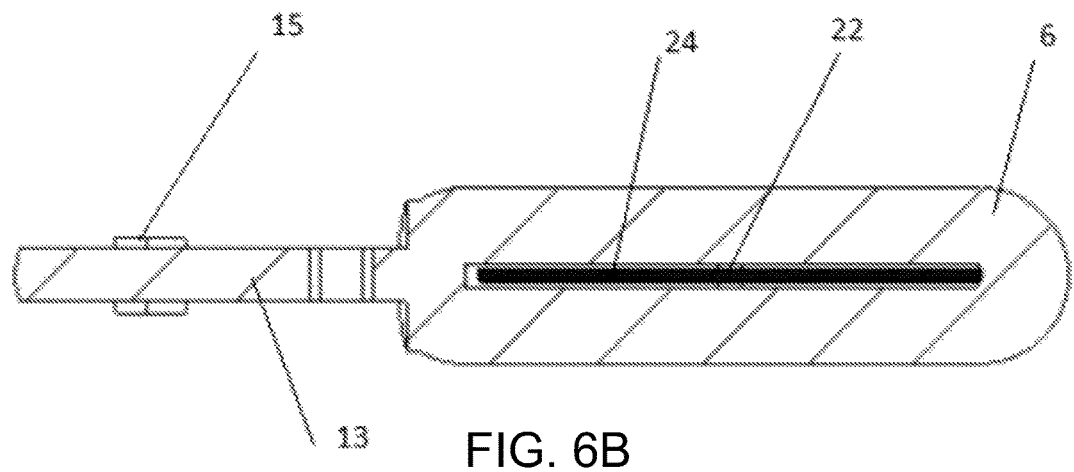
Figure 7A:
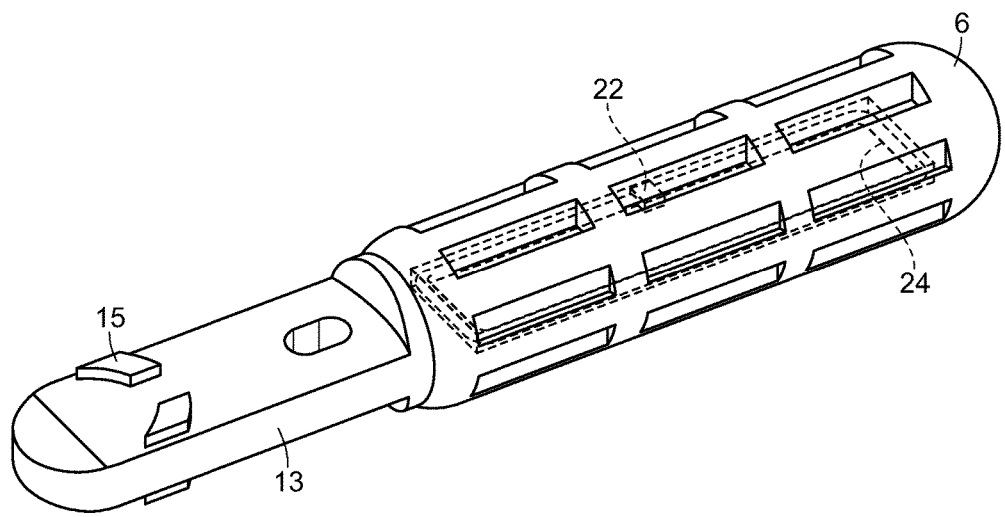
FIG. 7A and B show an illustration of one embodiment of an RFID tag inside the collecting element, where the RFID chip is on a loop antenna. A) is a three dimensional illustration, while B) is two dimensional illustration of the same.
Figure 7B:
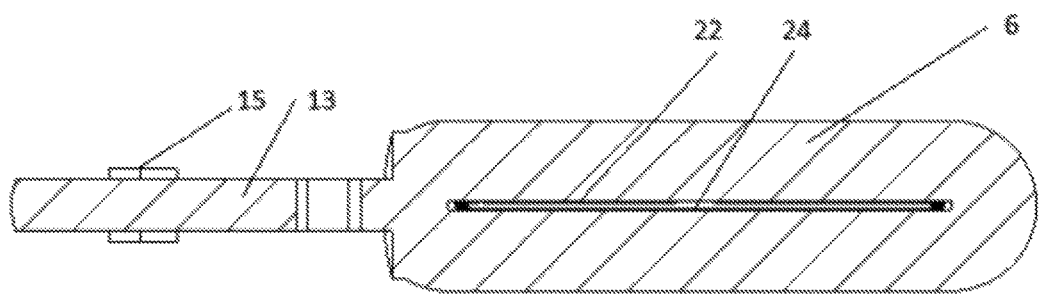
Figure 8:
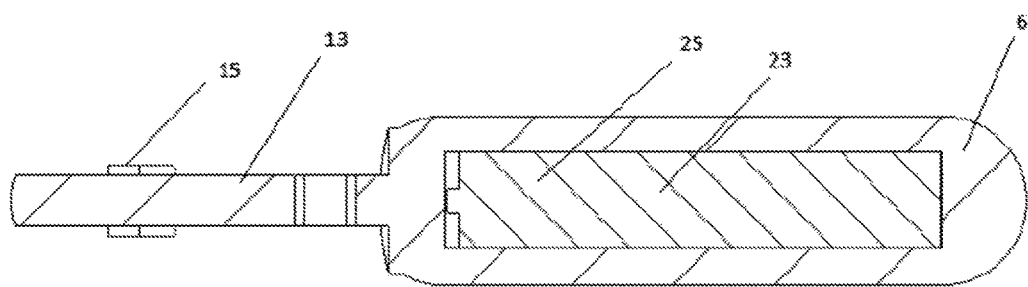
FIG. 8 shows an illustration of one embodiment of an RFID tag inside the collecting element, where the RFID tag is made of thin film and supported by a thicker non-flexible cylindrical substrate.
Figure 9A:
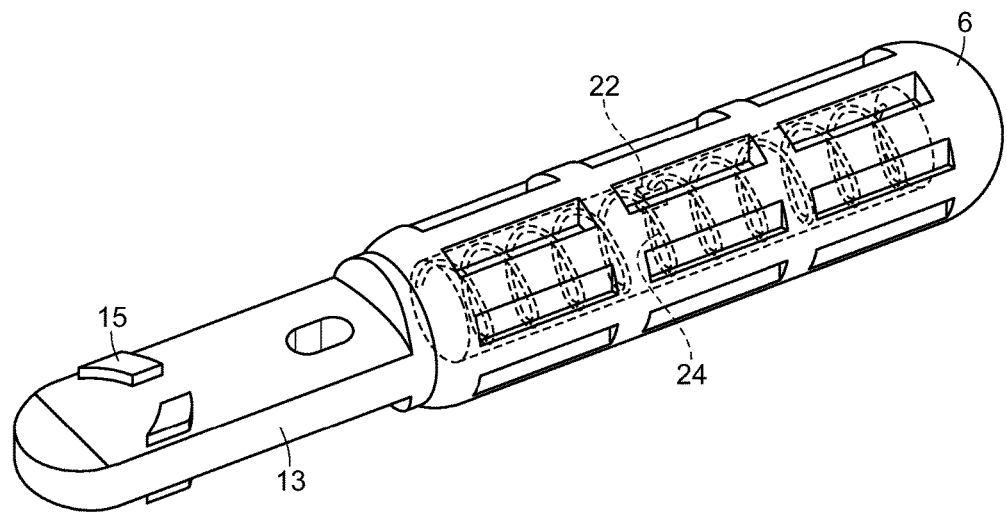
FIG. 9A and B show and illustration of one embodiment of the RFID tag inside the collecting element, where the RFID chip is on a helical coil antenna. A) is a three dimensional illustration, while B) is two dimensional illustration. The helical coil is shown here without a non-flexible cylindrical substrate such as shown in FIG. 8A and B, however such cylindrical substrate may be used with this embodiment as well.
Figure 9B:
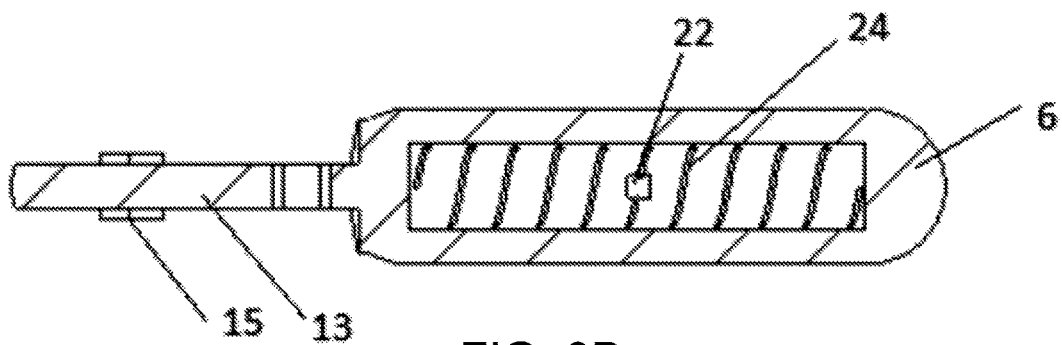

According to another embodiment the RFID tag may be encapsulated inside the sample collection element 6. This embodiment is illustrated in FIGS. 6-10. In FIG. 6A, and B an embodiment is shown where the RFID chip 22 inside the collecting element is on a thin metal wire antenna 24. In FIGS. 7A and B the RFID chip 22 inside the collecting element is on a metal wire antenna 24 formed to a loop antenna. In FIG. 8 the RFID chip 22 inside the collecting element is made on a thin film 23 (PET, PEN or PI) and supported by a thicker non-flexible cylindrical substrate 25 or directly on a PCB board. Alternatively, the RFID chip 22 may be directly attached to the cylindrical substrate 25 with wire. In FIG. 9A and B the RFID chip 22 inside the collecting element 6 is on a helical coil antenna 24. The helical coil is shown without a non-flexible cylindrical substrate such as hon in FIG. 8, however such cylindrical substrate may be used with this embodiment as well.

Figure 10A:
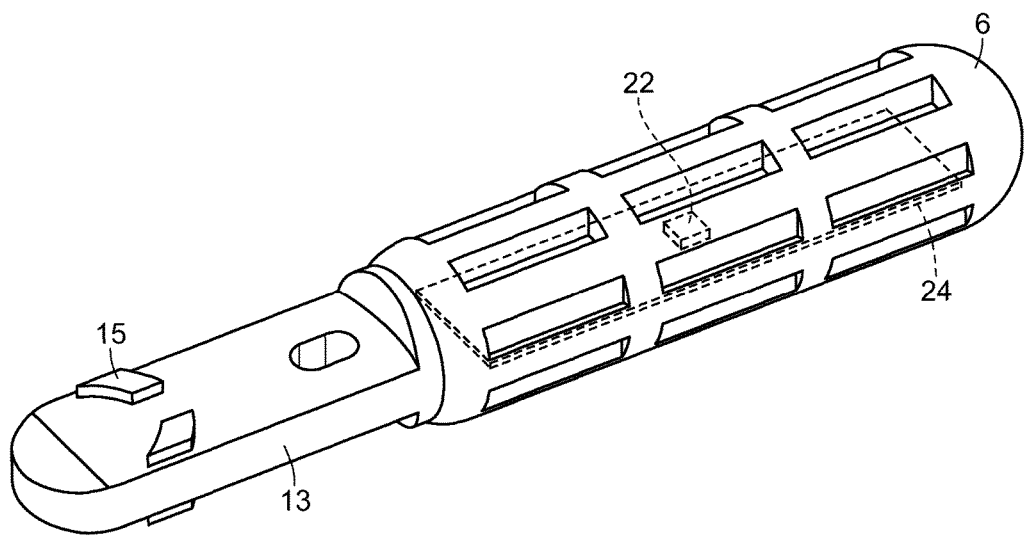
FIG. 10A and B show an illustration of one embodiment of the RFID tag inside the collecting element, where the RFID chip is on a plate antenna. A) is a three dimensional illustration, while B) is two dimensional illustration.
Figure 10B:
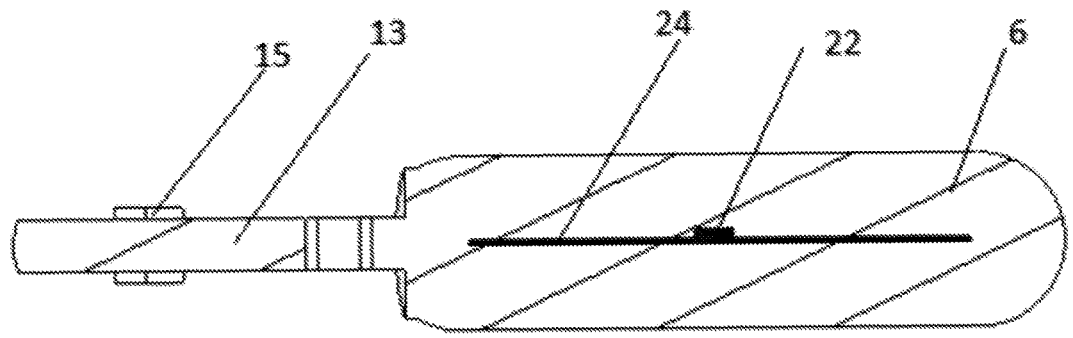

In FIG. 10 A and B the RFID chip 22 inside the collecting element is on a plate antenna 24. Typical structures are based on different kind of dipole antennas. In another embodiment the chip may be on a two layer plate antenna. Typical structures are based on patch antenna where two electrodes exist top to each other and where the substrate is good low glossy ceramic compound material According to one embodiment the plate antenna pattern (FIG. 10) and the cylindrical wire antenna pattern (FIG. 9) may also act as a secondary antenna where a commercial near field RFID tag is electromagnetically coupled.

The RFID tag is preferably a UHF-tag using approximately 860-960 mHz frequency. Other tagging technology may also be used (LF or HF), but the advantage of UHF tagging is that UHF makes it possible to achieve longer read distances. According to a preferred embodiment is to use UHF-tags in the collection portion of the sampling devices, thus enabling reading of a large number of collection portions from a distance up to several meters, preferably from about one meter, and most preferably from about 60 cm, in a closed box.

According to another embodiment the RFID tags may be read by smart phone using near field communication (NFC). In such case each tag is read separately. This embodiment is useful in situations where special reader equipment is not available.

Figure 5B:
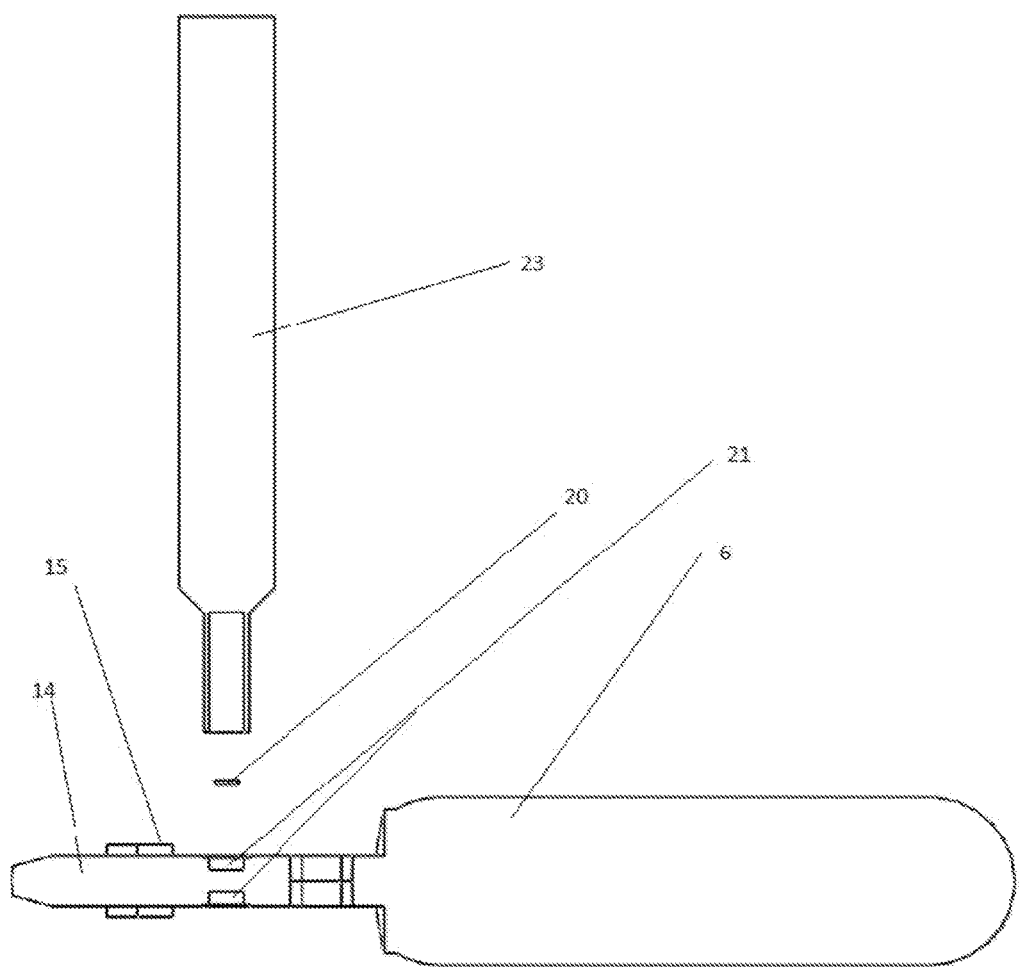

The RFID tags can be made to operate at any read distance between a few millimeters up to several meters. UHF-antenna may have both element, which would make it possible to use the same tag for near and far reading. As is shown in FIG. 5 A and B the RFID tag may be attached on the extension of the collecting element, but also other locations in the device could be used. In FIGS. 6-10 the tag is inside the collecting element. The advantage of having the RFID either on the extension of the collecting element or inside the collecting element, is that the RFID would always follow the sample and therefore eliminate the risk of losing identity of the sample and the patient data. When the RFID tag is injection molded into the collecting element, the system is specifically secure.

Moreover, the RFID tag in the extension of the collecting element or inside the collecting element eliminates the need of several barcoded labels on several parts of the kit (device, box, vial). Finally, the advantage in the RFID tag is that the tag would be less prone to damage than a barcode tag.

Now returning to FIGS. 3 and 4, the shaft 4, the absorbing sample collecting element 6, the sealable unit 7, and the unit cover 12 can be manufactured of any suitable materials as desired. For example, these components may be formed of the same or different plastic materials. In a further embodiment, a plastic material of the cell sampling device 2, preferentially polypropylene, is selected with a flexural modulus giving the shaft 4 flexibility to follow the anatomy of the vagina to reach portio vaginalis and at the same time rigid enough to get a close contact between the sample collecting element 6 and the mucous tissue ectocervix.

In a specific embodiment as shown in FIGS. 3A, 3B and 3H-3J, the sample collecting element 6 is generally cylindrical. The element 6 may be configured and sized as desired for a particular sample collection. In one embodiment, the element 6 is generally cylindrical as shown and has a diameter from about 2 to about 20 mm. In one embodiment as shown in FIGS. 3A, 3B, 3H and 3I, the front part of the sample collecting element 6 is rounded and may be made very smooth, so as to render it more tissue friendly and easier for introduction into the sensitive tissue of the vagina.

In a further embodiment, the sample collecting element 6 comprises at least one raised portion 9. In another embodiment, the raised portions of the sample collecting element 6 form a plurality of cell and mucous adsorbing segments 10. The segments 10 are separated by at least one groove 11 or a plurality of grooves 11. In a specific embodiment, the grooves 11 are from about 0.01 to 4 mm in width and in another embodiment, the raised portions 9 include an edge at the groove 11 capable of scraping tissue to collect a sample. In an additional embodiment, the raised portions 9 forming the segments 10 and the grooves 11 are configured to collect a cell sample and hold the sample within the grooves 11 even during withdrawal of the device 2 from a body orifice. In a specific embodiment, the segments 10 of the sample collecting element 6 have an unpolished surface and, in a specific embodiment, comprise an abrasive surface, for example having a surface roughness of about 1 to 100 μm, to facilitate release of cell-containing mucous, for example, from ectocervix tissue.

In one embodiment, the raised portions 9 form segments 10 which are essentially rectangular in shape by providing the grooves 11 in the longitudinal and transversal directions on the sample collecting element 6. However, it is of course possible to provide grooves 11 in other geometries, e.g. in spiral or zigzag patterns. In one embodiment, the grooves 11 are substantially narrower than the width of the raised portions 9. In one embodiment the width of the grooves 11 does not exceed about 4 mm, and in another embodiment, the width is from about 0.5 to about 0.1 mm. Importantly, the grooves 11 should be able to absorb mucous liquid and cells therein, and maintain these materials in place during retraction of the device from the body orifice.

Figure 2:
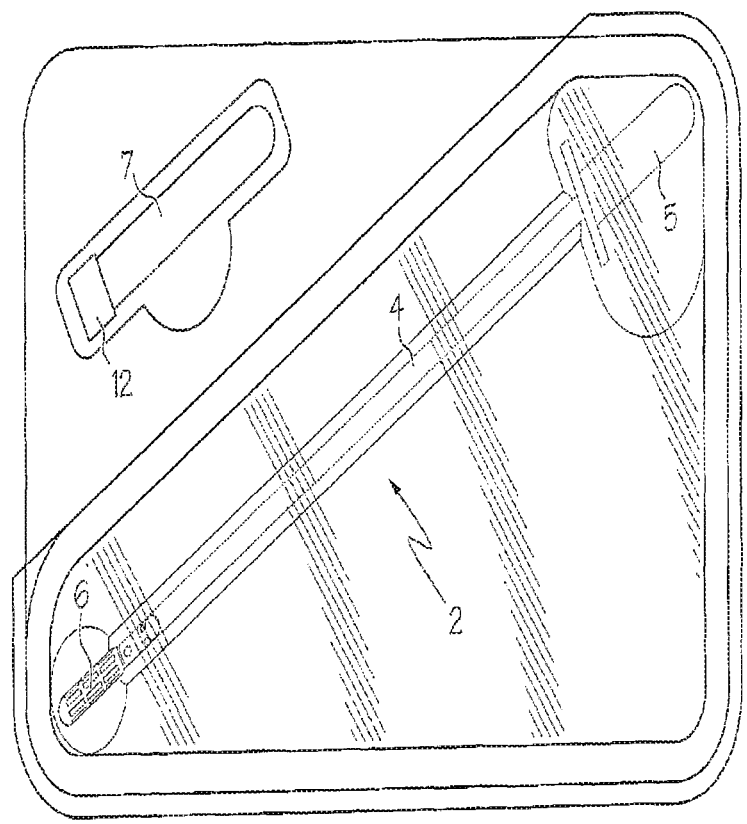
FIG. 2 is a top view of a sampling device and a sealable unit held in a protective plastic tray, in accordance with one embodiment of the sampling system of the invention.

The sample collecting element 6 is removably connected with one end of the shaft 4. Thus, the sample collecting element 6 may be connected with the shaft 4 to facilitate obtaining a mucous sample, for example from ectocervix tissue, and may then be removed from the shaft 4 for insertion in the sealable unit 7. One of ordinary skill in the art will appreciate that various connection configurations may be employed to facilitate the removable connection of the sample collecting element 6 with the end of the shaft 4. In the specific embodiments shown in FIG. 3A-3J, an end of the sample collecting element 6 is provided with an extension 13 having protrusions 15. The end of the shaft 4 is correspondingly provided with extensions 16 having grooves adapted to receive protrusions 15 therein in a snap-fit manner. Thus, the extension 13 is inserted between the extensions 16 in a male-female type manner in which the protrusions 15 are snap fit within grooves contained in the extension 16 at the end of the shaft 4. According to one embodiment the shaft extension 16 have a protrusion 16a fitting to a groove or hole 16b in the collecting element extension 13, thereby securing the collecting element to the shaft extension while taking the sample. The protrusions are released from the grooves contained in extension 16 by rotation of the sample collecting element 6 as shown in FIG. 3B. As a result, the sample collecting element 6 may be removed from the shaft 4 to the unit 7 and preferably sealed therein, for example with a unit cover 12 as shown in FIG. 2. Advantageously, to prevent contamination of the sample collecting element 6 once a mucous sample is adhered thereto, the sample collecting element 6 may be at least partially inserted within the unit 7, prior to removal of the sample collecting element 6 from the shaft 4. The unit 7 may then be moved to rotate the sample collecting element 6 as shown in FIG. 3B and release the sample collecting element 6 from extension 16 of the shaft 4. After release of the sample collecting element 6 from its connection with the shaft 4, the remainder of the sample collecting element 6 is then inserted into the unit 7, for example by gravity by holding the sample collection unit an upright vertical position, or by pushing the sample collected element further into the unit with the end of the shaft 4. The unit 7 is then sealed with the appropriate cover, preferably to form an airtight seal.

The sealed unit 7, having the sample collecting element 6 therein, may then be placed in the mailing package 14 which is designed to protect the sealed unit 7 during return transport of the sealed unit to a medical facility, for example a doctor's office, hospital or laboratory, for appropriate testing of the collected sample therein.

In one embodiment, the sample collecting system further comprises an instruction sheet, particularly useful when the sampling system is adapted for self-sampling by an individual.

In one embodiment, the sampling system of the invention is configured to allow an individual to self-collect a sample. In an additional embodiment, the self-sampling device is configured to allow an individual to collect a sample from mucous tissue. In another embodiment, the mucous tissue resides in the gynecological tract and in another embodiment the mucous tissue resides in the mouth, (e.g. cheek). The sampling system may be used by distribution to a patient, who conducts sampling and returns the sample for final laboratory analysis according to the present invention.

EXAMPLE 1

This example examines if the same result will be obtained when gynecological smears are taken by hospital staff using previous standard procedures or using the sampling system according to the present invention, as well as if patients themselves use the sampling system.

Figure 4:
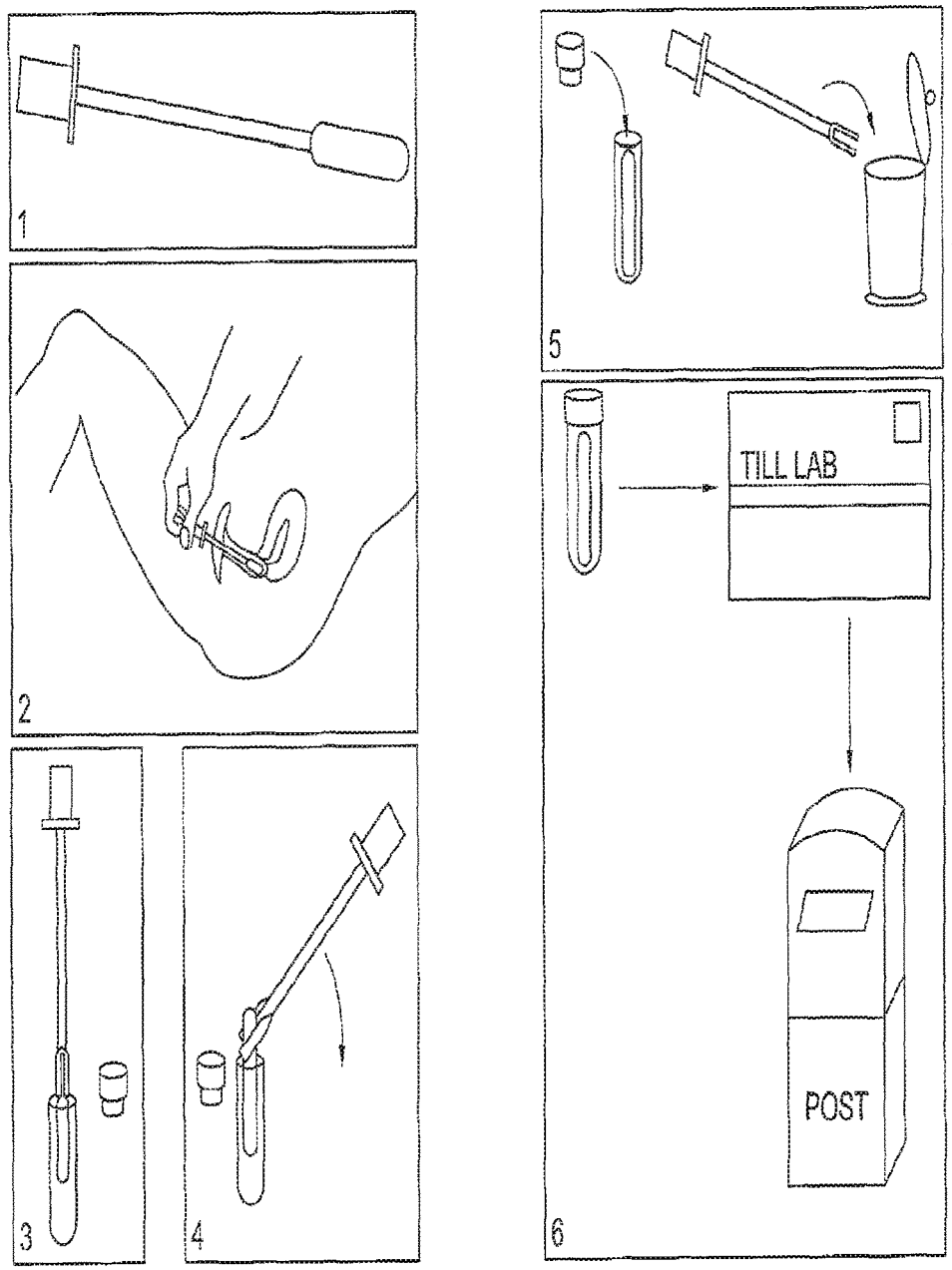
FIG. 4 is an illustration of an instruction sheet suitable for use in accordance with one embodiment of the sampling system of the invention.

Thirty six women were requested to come to the hospital for regular gynecological control and participate in the study. The hospital staff secured gynecological smears from the portio area with the use of a cytobrush. One sample is used for conventional cytological screening and the other for HPV analysis. The women took one sample themselves with the present invention following the written information as shown in FIG. 4. This sample was used for HPV analysis.

All samples were sent to the Department of Pathology, University of Uppsala. The smears collected with cytobrush by the gynecological staff and the smears collected by the women themselves with the device were analyzed for presence of HPV with the Hybrid Capture II method (Digene Diagnostics Inc., Silver Spring, Md., USA). The cytological smears were, after screening, examined for HPV using a PCR based technique.

All samples taken with previous standard procedures were scraped into test tubes and PCR buffer and proteinase K is added. When samples were taken with the device according to the present invention, the PCR buffer and proteinase K were simply added into the sealable unit, either by the user, or prior to delivery of the sampling system to a user, or upon return of the unit to, for example, a testing facility. The cells were digested at 60° C. and the DNA fraction recovered with standard methods.

The PCR amplification was performed in 100 µl volume containing standard amplification reagents. Type-specific PCR amplification was performed under conditions described by Brule et al. using GP5+/GP6+ general primers. Samples with HPV DNA amplicones were sequenced with an ABI PRISM 310 Genetic Analyzer (Applied Biosystems, Foster City, Calif.) after which the HPV type can be determined.

The results from these studies demonstrated (results not shown) that the women themselves can readily secure gynecological samples with the device according to the present invention. Furthermore, both cytological and PCR analysis of the samples gave essentially the same result as when medical staff took the samples either using the present device or other previously well-established sampling methods. It is demonstrated that the analysis can be carried out with satisfactory results three days after sampling with the device.

Thus, the sampling system is particularly advantageous for self-sampling for gynecological samples, and particularly HPV analysis. After self-sampling at home, the device may be rapidly returned by mail to a hospital laboratory for HPV analysis. The sampling system according to the present invention is surprisingly well accepted, and is particularly useful for self-sampling at home.

The sampling system will increase participation in the gynecological screening programs evaluating the risk of developing cervical cancer in situ. Self and home sampling will be positive from a health-economic point of view, but more importantly, increased participation will decrease the incidence of cervical cancer and also decrease the number of women who die of this disease.

The specific illustrations and embodiments described herein are exemplary only in nature and are not intended to be limiting of the invention defined by the claims. Further embodiments and examples will be apparent to one of ordinary skill in the art in view of this specification and are within the scope of the claimed invention.

EXAMPLE 2

The identification tag, be it a bar code attached to the envelope and the device as described above, or an RFID tag attached to the device as described above, may include information related to the manufacture and the device, but the information may also include information of the patient. In case of a device including an RFID tag, the tag may include several layers of information and part of the information may be written on the tag by the manufacturer.

Figure 11:
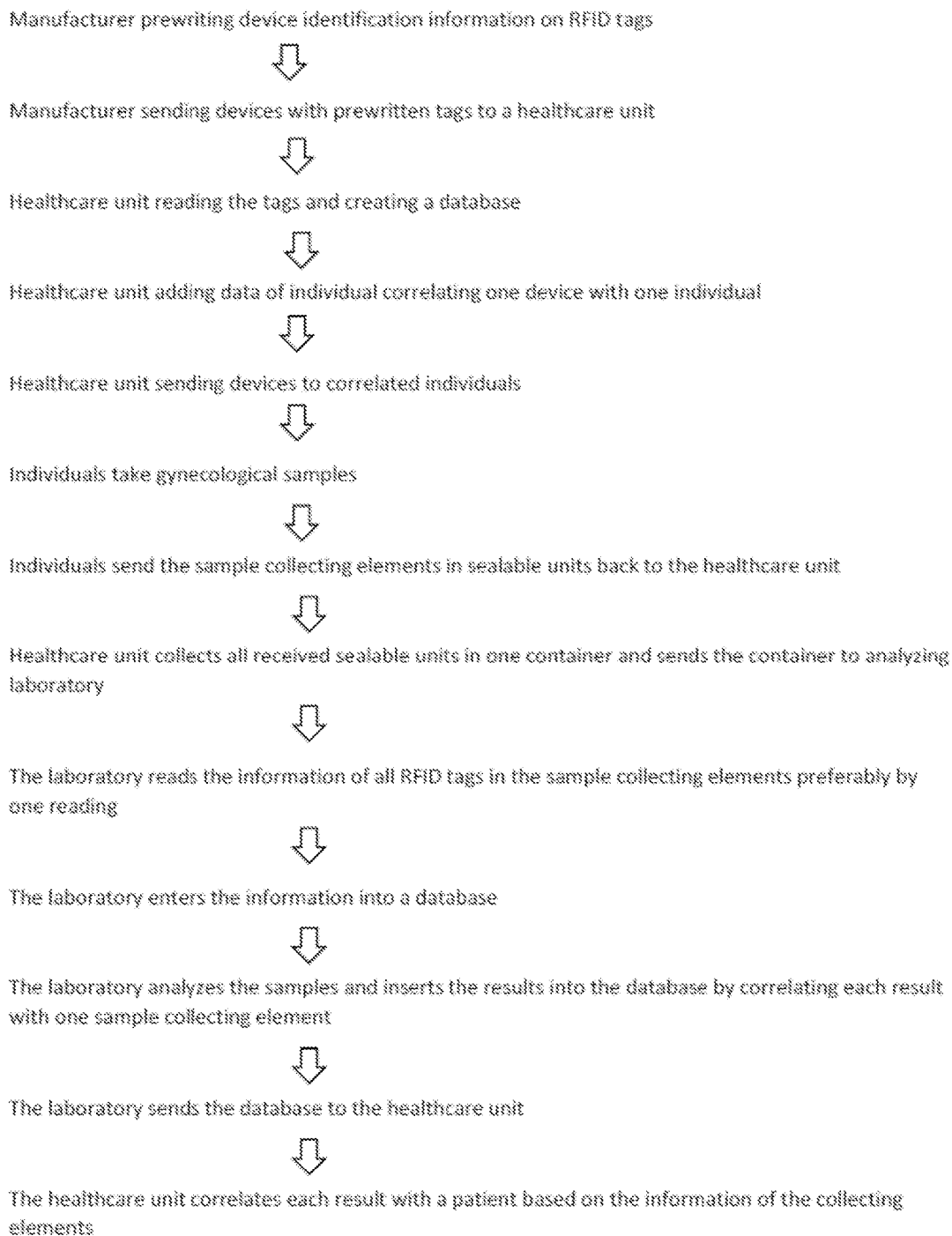
FIG. 11 illustrates a logistic chain of the from a manufacturer devices with prewritten information data, to a healthcare unit which creates a database correlating an individual with each device and send the devices to the individuals using the sampling devices, the individuals sending the samples back to the healthcare unit which is sending a large number of received samples to a laboratory; the laboratory testing the samples and correlating results with the devices based on the identification information on the ID tag of the device, sending the results to the healthcare unit which correlates the results with the individuals based on the databases The embodiments set forth in the drawings are illustrative in nature and are not intended to be limiting of the invention defined by the claims. Moreover, individual features of the drawings and the invention will be more fully apparent and understood in view of the following detailed description.

A typical situation, which is illustrated in FIG. 11, would be where the manufacturer includes information of the device on RFID-tags. The manufacturer may send the devices and the prewritten RFID tags to a hospital or other user. The hospital may read the information of all the tags by one reading and enter the information into their database. The hospital may then write additional data on its database, which can connect to the RFID tag, for example patient's name, age, address and so on. The hospital and or laboratories collects a large number of samples sent from a number of individuals and inserts all the samples into one box, which is sent to the laboratory for analysis. Now the laboratory can read all of the samples contained in the box with one reading simultaneously. The laboratory personnel will set the samples on trays and trays can be brought to an automatic analyzing device. Each sample can be read before going to the analyzing device and the information of the analysis can be entered into a database without any further organization of the samples once taken from the box and set on the tray. In addition, even if the samples have not been read previously, the entire tray can at this point be read with one reading.

The information, patient and analysis data including the result is instantly stored in a database and may then be sent to the hospital electronically or in hard format. The tracking system including the RFID tag makes the logistics and processing of the samples and of the information related to the samples much easier than any previously used method.

What is claimed is:

1. A cervical self-sampling system comprising:
   a) a mailing package; and
   b) a self-sampling device consisting of:
      a. a flexible linear shaft configured to allow an individual to self-collect a sample from cervical mucous tissue, said shaft having a first end and a second end and a handle at the first end and a longitudinal axis extending from the first end to the second end, and the second end having a shaft extension with two perpendicular prongs;
      b. a detachable cylindrical sample collecting element having a rounded distal end and a collecting element extension at a proximate end, the collecting element extension dimensioned to fit in between the two prongs of the shaft extension, wherein the sample collecting element is detachably connected to the shaft extension by snapping the collecting element extension in between the prongs of the shaft extension, the colleting element including an RFID-tag having an RFID-chip and an antenna, and wherein the collecting element has a surface formed of raised portions and grooves, the grooves being arranged on the collecting element surface as elongated wells in several parallel rows surrounded by the raised portions, and wherein the grooves have a width ranging from 0.1 to 4 mm, the surface of the collecting element has surface roughness of 1 to 100 µm, and the grooves are capable of holding a cervical sample for satisfactory laboratory analysis for up to three days after sampling; and
      c. a closable empty container, wherein the container is configured to store the sample collecting element, disconnected from the shaft and having a sample thereon.

2. The system of claim 1, wherein the RFID-tag locates in the collecting element extension.

3. The system of claim 2, wherein the collecting element extension is flat and has a first flat side and a second flat side and each flat side contains one cavity for adapting the RFID-tag.

4. The system of claim 3, wherein the RFID -tag is inserted into either one of the two cavities on the collecting element extension.

5. The system of claim 1, wherein the RFID tag locates inside the collecting element.

6. The system of claim 1, wherein an RFID reader can read information on the RFID-tag from 1 mm to 1 m distance.

7. The system of claim 1, wherein the antenna is a loop antenna.

8. The system of claim 1, wherein the antenna is a plate antenna.

9. The system of claim 1, wherein the antenna is a coil antenna.

10. The system of claim 1, wherein the tag is on a film supported by a cylindrical substrate.

11. A logistic method for gynecological samples, comprising the steps of:
   a) Providing to a healthcare unit a multitude of self-sampling systems, each system comprising a self-sampling devices and a closable container, the device comprising a shaft and a sample collecting element removably attachable to the shaft, and the sample collecting element comprising a prewritten RFID-tag containing information to identify the device, and wherein the collecting element has a surface formed of raised portions and grooves, the grooves being arranged on the collecting element surface as elongated wells in several parallel rows surrounds by the raised portions, and wherein the grooves have a width ranging from 0.1 to 4 mm, the surface of the collecting elements has surface roughness of 1 to 100 µm, and the grooves are capable of holding a cervical sample for satisfactory laboratory analysis for up to three days after sampling, and the closable container being configured to store the sample collecting element when disconnected from the shaft and having a sample thereon;
   b) the healthcare unit reading the information of each device and entering the information into a healthcare unit database;
   c) the healthcare unit adding information of a multitude of individuals on the healthcare unit database and correlating one device with one individual;
   d) the healthcare unit sending each system to the individual correlated with the device in step c);
   e) the individual, upon receive of the device, self-sampling a mucous sample, inserting the sample collecting element into the closable container and sending the closable container back to the healthcare unit;
   f) the healthcare unit collecting all received closable containers containing samples for analysis for a same condition into a single container and sending the single container to a laboratory;
   g) the laboratory reading the information of all the received closable containers in the single container with one reading of the RFID-tags;
   h) the laboratory entering the read information into a laboratory database;
   i) the laboratory analyzing the samples of the single container for the same condition and entering the results into the laboratory database by correlating one result with one device information;
   j) the laboratory sending the information in the laboratory database to the healthcare unit;
   k the healthcare unit correlating each result with individuals based on the device information recorded in step b); and
   l) the healthcare unit informing each individual of her result.

12. The method of claim 11, wherein sample is a cervical sample and the condition analyzed in step i) is Human Papilloma Virus infection.

13. The method of claim 11, wherein the RFID-tag locates in an extension of the collecting element.

14. The method of claim 11, wherein the RFID tag locates inside the collecting element.

* * * * *